US010068678B2

(12) United States Patent
Liu (10) Patent No.: US 10,068,678 B2
(45) Date of Patent: *Sep. 4, 2018

(54) X-RAY IMAGING SYSTEM WITH A MOTORLESS REAL-TIME CONTROLLABLE COLLIMATOR THAT CAN PRODUCE ARBITRARILY SHAPED X-RAY BEAMS

(71) Applicant: General Electric Company, Schenectady, NY (US)

(72) Inventor: James Liu, Salt Lake City, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 317 days.

This patent is subject to a terminal disclaimer.

(21) Appl. No.: 14/985,919

(22) Filed: Dec. 31, 2015

(65) Prior Publication Data

US 2016/0189817 A1 Jun. 30, 2016

Related U.S. Application Data

(60) Provisional application No. 62/098,840, filed on Dec. 31, 2014.

(51) Int. Cl.
*A61B 6/06* (2006.01)
*G21K 1/04* (2006.01)
*A61B 6/00* (2006.01)

(52) U.S. Cl.
CPC ............ *G21K 1/04* (2013.01); *A61B 6/06* (2013.01); *A61B 6/488* (2013.01); *A61B 6/542* (2013.01);

(Continued)

(58) Field of Classification Search
CPC .. A61B 6/00; A61B 6/06; A61B 6/405; A61B 6/488; A61B 6/52; A61B 6/54; A61B 6/542; A61B 6/545; A61B 6/547; A61B 6/582; A61B 2560/00; A61B 2560/02; A61B 2560/0266; A61B 2562/00; A61B 2576/00; G06T 1/00; G06T 1/0007;

(Continued)

(56) References Cited

U.S. PATENT DOCUMENTS 6,061,426 A * 5/2000 Linders ............... G21K 1/10
378/149
2008/0063141 A1* 3/2008 Luan ................... A61N 5/1042
378/65

(Continued)

*Primary Examiner* — Anastasia Midkiff (57) ABSTRACT

An X-ray imaging system including an X-ray source, a motorless real-time controllable 3D X-ray collimator, a digital X-ray detector, and a system controller coupled to the X-ray radiation source, the motorless real-time controllable 3D X-ray collimator, and the digital X-ray detector for controlling the motorless real-time 3D X-ray collimator to reduce X-ray radiation dose and improve image quality. The motorless real-time controllable 3D X-ray collimator includes a top panel, a bottom panel, at least one sidewall joining the top panel to the bottom panel, an open area between the top panel, bottom panel, and at least one 2D pixel array coupled to at least one of the top panel and the bottom panel, the at least one 2D pixel array having a plurality of pixels of thin film electric coils and switching thin film field-effect transistors, wherein the open area is at least partially filled with a mixture of ferromagnetic material and high X-ray attenuation material.

16 Claims, 6 Drawing Sheets

(52) U.S. Cl.
CPC ............................ *A61B 2560/0266* (2013.01); *G01N 2223/316* (2013.01); *G21K 1/046* (2013.01)

(58) Field of Classification Search
CPC ....... G06T 1/0014; G06T 7/00; G06T 7/0012; G06T 7/0014; G06T 7/0016; G06T 11/00; G06T 11/003; G06T 11/005; G06T 2200/28; G06T 2207/00; G06T 2207/10; G06T 2207/10072; G06T 2207/10081; G06T 2207/20; G06T 2207/20004; G21K 1/00; G21K 1/02; G21K 1/04; G21K 1/046; G21K 5/00; G21K 5/10; G21K 2210/00; G21K 2210/41; G21K 2211/00; G21K 2211/40; G21K 2211/412; G21K 2211/424; G01N 2223/00; G01N 2223/303; G01N 2223/316; G01N 2223/40; G01N 2223/402; G01N 2223/405; G01N 2223/419; A61N 5/00; A61N 5/10; A61N 5/103; A61N 5/1042; A61N 5/1045; A61N 5/1048; A61N 5/1064; A61N 5/1065; H05G 1/26; H05G 1/30; G01T 1/00; G01T 1/16; G01T 1/1606; G01T 1/29; G01T 1/2914
See application file for complete search history.

(56) References Cited

U.S. PATENT DOCUMENTS

| | | | |
|---|---|---|---|
| 2013/0202091 A1* | 8/2013 | Haider | G21K 1/046 378/145 |
| 2013/0202092 A1* | 8/2013 | Haider | G21K 1/04 378/145 |
| 2014/0110604 A1* | 4/2014 | Ein-Gal | G21F 3/00 250/492.1 |
| 2015/0272532 A1* | 10/2015 | Allmendinger | A61B 6/032 600/427 |
| 2016/0189818 A1* | 6/2016 | Liu | G21K 1/10 378/147 |

* cited by examiner

X-RAY IMAGING SYSTEM WITH A MOTORLESS REAL-TIME CONTROLLABLE COLLIMATOR THAT CAN PRODUCE ARBITRARILY SHAPED X-RAY BEAMS

CROSS-REFERENCE TO RELATED APPLICATIONS

This application claims the benefit of U.S. Provisional Patent Application No. 62/098,840, filed on Dec. 31, 2014, the entirety of which is incorporated herein by reference.

BACKGROUND

This disclosure relates generally to X-ray imaging systems and methods, and more particularly to X-ray imaging system and method with a motorless real-time controllable three-dimensional (3D) X-ray collimator that blocks certain portions of an X-ray beam to produce arbitrarily shaped X-ray beams.

A collimator is an important component in an X-ray imaging system. The collimator is used to form the shape of an X-ray beam such that only the necessary region of patient anatomy is radiated by the X-ray beam. Existing collimators produce an X-ray beam having either a rectangular shape or a nearly circular shape or the combination of the two shapes. The rectangular shaped X-ray beam is formed by collimator blades, while the circular shaped X-ray beam is formed by a collimator iris. Usually, the collimator blades and iris are driven by electric motors.

Current X-ray imaging systems have two major disadvantages. First, the region of interest of the patient's anatomy may have different shapes. With an existing collimator, a larger area of anatomy is radiated by an X-ray beam to cover the region of interest. Second, X-ray radiation is exposed to the X-ray detector, which not only reduces the life of the X-ray detector but also introduces image artifacts such as lag and gain hysteresis. In addition, the use of electric motors degrades the reliability of the X-ray imaging system.

The present discloser discloses a motorless real-time controllable 3D X-ray collimator that forms an X-ray beam with arbitrarily desirable shapes without an electric motor. The 3D X-ray collimator overcomes the aforementioned disadvantages of existing collimator technology. With proper system and method control mechanisms, this disclosure can reduce X-ray radiation dose to the patient, enhance image quality, and improve X-ray imaging system and method reliability.

BRIEF DESCRIPTION

In accordance with an aspect of the present disclosure, an X-ray imaging system comprising an X-ray source that emits X-ray radiation; a motorless real-time controllable 3D X-ray collimator; a digital X-ray detector; and a system controller coupled to the X-ray source, the a motorless real-time controllable 3D X-ray collimator, and the digital X-ray detector for controlling the motorless real-time controllable 3D X-ray collimator to reduce X-ray radiation dose and improve image quality.

In accordance with an aspect of the present disclosure, a motorless real-time controllable 3D X-ray collimator comprising a top panel; a bottom panel; at least one sidewall joining the top panel to the bottom panel; an open area between the top panel, bottom panel, and at least one sidewall; and at least one 2D pixel array coupled to at least one of the top panel and the bottom panel, the at least one 2D pixel array having a plurality of pixels of thin film electric coils and switching thin film field-effect transistors; wherein the open area is at least partially filled with a mixture of ferromagnetic material and high X-ray attenuation material.

In accordance with an aspect of the present disclosure, a method of controlling a 3D X-ray collimator in real-time, the method comprising the steps of acquiring a pre-acquisition image or an image frame from an X-ray imaging system; dividing the pre-acquisition image or image frame into N×N regions through the use of an image processing system; determining the average X-ray image intensity in each N×N region to create a 2D X-ray image intensity map; determining the desired X-ray collimation in each N×N region from the average X-ray image intensity in each N×N region; and using the desired X-ray collimation in each N×N region of the 2D X-ray image intensity map to control current applied to each coil of the 3D X-ray collimator.

Various other features, aspects, and advantages will be made apparent to those skilled in the art from the accompanying drawings and detailed description thereof.

DETAILED DESCRIPTION

Figure 1:
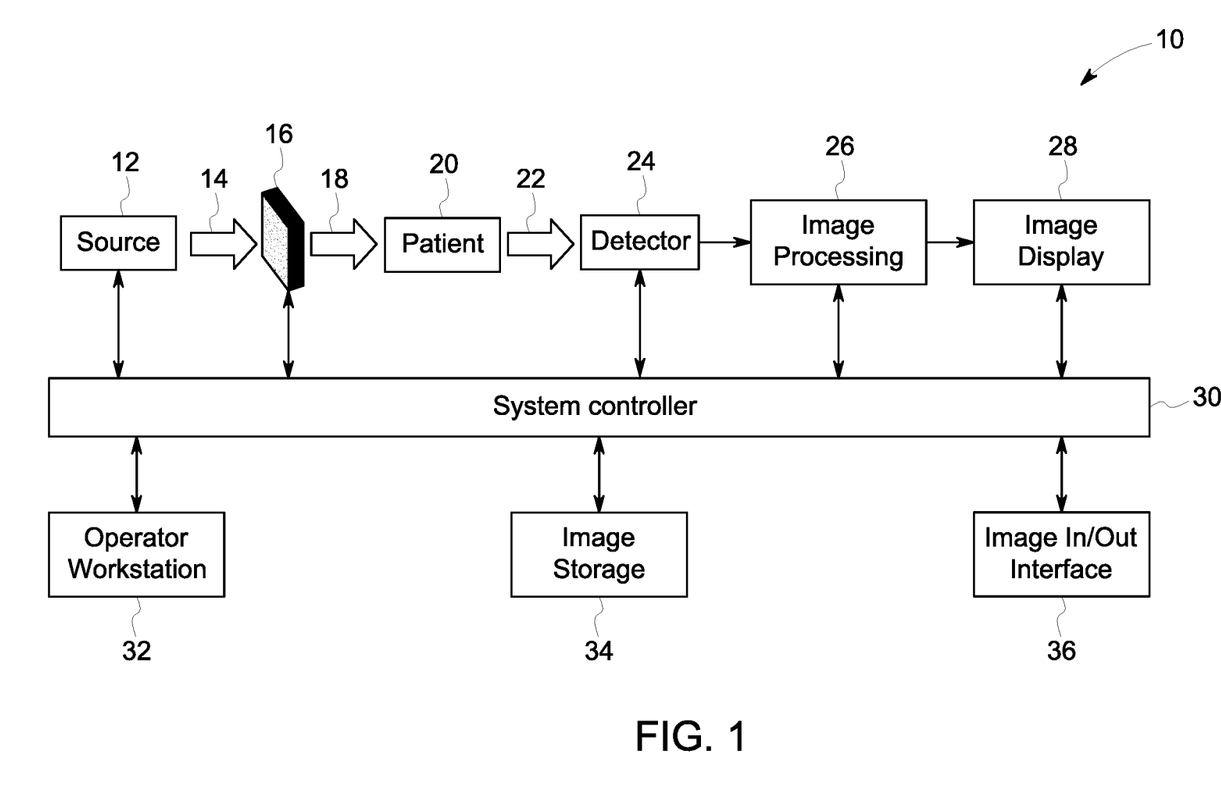
FIG. 1 is a block diagram of an exemplary embodiment of an X-ray imaging system.

Referring generally to FIG. 1, an X-ray imaging system is represented and referenced generally by reference numeral 10. In the illustrated embodiment, the X-ray imaging system 10, as adapted, is a digital X-ray imaging system. The X-ray imaging system 10 is designed both to acquire image data and to process the image data for display in accordance with the present technique. Throughout the following discussion, however, while basic and background information is provided on the digital X-ray imaging system used in medical diagnostic applications, it should be born in mind that aspects of the present techniques may be applied to X-ray imaging systems, used in different settings (e.g., projection X-ray imaging, computed tomography imaging, tomosynthesis imaging, fluoroscopic imaging, mammographic imaging, radiographic imaging, etc.) and for different purposes (e.g., parcel, baggage, vehicle and component inspection, etc.).

FIG. 1 illustrates a block diagram of an exemplary embodiment of an X-ray imaging system 10. The X-ray imaging system 10 includes an X-ray source 12 that emits X-ray radiation 14 and a motorless real-time controllable 3D X-ray collimator 16. The X-ray collimator 16 blocks a portion of the X-ray beam 14 coming from the X-ray source 12. The collimated X-ray beam 18 is directed into a region in which a subject 20, such as a human patient, an animal or an object, is positioned. A portion of the X-ray beam 18 passes through the subject 20 and impacts a digital X-ray detector 24. The digital X-ray detector 24 converts X-ray photons received on the surface of an X-ray detector panel array (not shown) to lower energy photons, and subsequently to electric signals which are acquired and processed by an image processing system 26 to reconstruct an image of the subject features or anatomy on an image display 28. The beam of X-ray radiation 18 is uniformly radiated on a field of view of the subject 20 or patient anatomy being imaged. The probability of X-ray radiation 18 being absorbed by the subject 20 or patient anatomy depends on two things. One is the energy of the X-ray radiation 18 and the other is the property of the matter in the path of the X-ray radiation 18 including the thickness, density, and type of matter of the patient's anatomy. Thus, the X-ray beam 22 after traveling through the subject 20 reflects the thickness and the type of matter inside the subject 20 or patient anatomy.

In the embodiment illustrated in FIG. 1, the X-ray imaging system 10 may be a stationary X-ray imaging system disposed in a fixed X-ray imaging room. It will be appreciated, however, that the presently disclosed techniques may also be employed with other X-ray imaging systems, including a mobile X-ray imaging system in other embodiments.

Imagine that if all the X-ray photons in the X-ray radiation beam 18 are absorbed by the subject 20 or patient anatomy, we would have a flat image without any anatomical information because all the pixels in the image would have exactly the same value. On the other hand, if all the X-ray photons in the X-ray radiation beam 18 penetrate through the subject 20 or patient without being absorbed, we would not have any anatomical information for the same reason.

The X-ray source 12, the motorless real-time controllable 3D X-ray collimator 16, digital X-ray detector 24, image processing system 26, and image display 28 may be coupled to the system controller 30. The system controller 30 may include a power supply, collimator controller, detector controller and at least one processor and memory. The at least one processor, memory, detector controller, collimator controller, source controller, and all of the electronics and circuitry within these components may receive power from the power supply. The memory may store various configuration parameters, calibration files, and detector identification data. In addition, the memory may store patient information to be combined with the image data to generate a DICOM compliant data file. In an exemplary embodiment, the X-ray source 12 may be coupled to an X-ray source controller, which may be part of the system controller 30 configured to command X-ray emission of X-rays for image exposures. In an exemplary embodiment, the power supply may include one or more batteries.

The system controller 30, memory, and processor may be coupled to an operator workstation 32, image storage system 34, and image in/out interface 36. The system controller 30 may be in communication with the operator workstation 32, image storage system 34, and image in/out interface 36 over a network via the wired or wireless connection. The system controller 30 may be configured to wirelessly transmit or transmit through a wired connection partially processed or fully processed X-ray image data to the image storage system 34. The image storage system 34 may include a picture archiving and communication system (PACS), a radiology information system (RIS), and/or a hospital information system (HIS). The image storage system 34 may store sampled data gathered during the imaging mode as well as X-ray image data.

Figure 2:
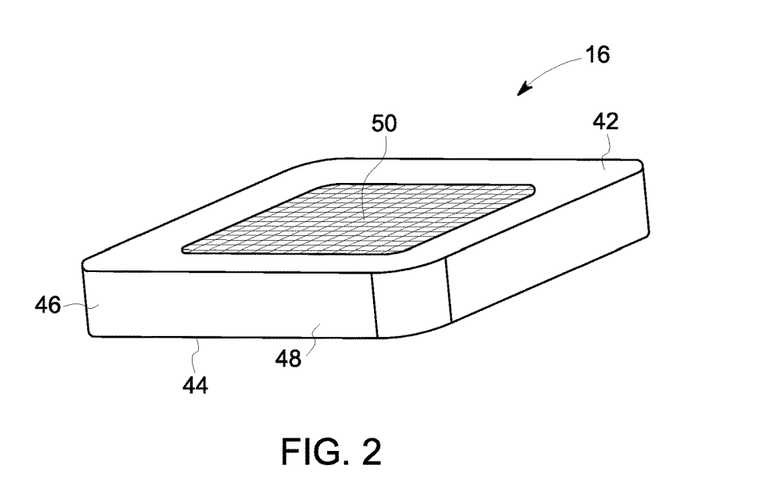
FIG. 2 is a schematic diagram of an exemplary embodiment of a motorless real-time controllable 3D X-ray collimator.

FIG. 2 illustrates a schematic diagram of an exemplary embodiment of a motorless real-time controllable 3D X-ray collimator 16. The motorless real-time controllable 3D X-ray collimator 16 includes a top panel 42, a bottom panel 44, at least one sidewall 46 joining the top panel 42 to the bottom panel 44, and an open area 48 between the top panel 42, bottom panel 44, and at least one sidewall 46. The top panel 42 and the bottom panel 44 are spaced apart from each other by the at least one sidewall 46 and are parallel with each other. In an exemplary embodiment, the top panel 42, bottom panel 44, and at least one sidewall 46 may be made of a low X-ray attenuation material such as glass, carbon fiber, aluminum, etc. The open area 48 is at least partially filled with a mixture of ferromagnetic material and high X-ray attenuation material (not shown). The mixture of ferromagnetic material and high X-ray attenuation material blocks a portion of the beam of X-ray radiation 14. The 3D X-ray collimator 16 blocks a portion of X-ray radiation dose to the patient 20. The total X-ray collimation of the mixture of ferromagnetic material and high X-ray attenuation material depends on the X-ray attenuation of each material as well as the percentage of each material used.

The mixture of ferromagnetic material and high X-ray attenuation material may be in the form of solid material or liquid material. In an exemplary embodiment, the mixture may include a plurality of tiny metallic balls made of a ferromagnetic material such as iron (Fe) and neodymium (Nd) mixed with a high X-ray attenuation material such as tungsten (W) and lead (Pb). In a preferred embodiment, the diameter of the tiny metallic balls shall be as small as possible, typically, in the range of micrometers to tens of micrometers.

In another exemplary embodiment, the mixture of ferromagnetic material and high X-ray attenuation material may be in the form of a liquid (ferrofluid). A ferrofluid is a liquid that becomes strongly magnetized in the presence of a magnetic field. In a preferred embodiment, the ferrofluid may be made from nanostructured particles of ferromagnetic and high X-ray attenuation materials such as iron (Fe) and neodymium (Nd) suspended in a carrier fluid such as mercury (Hg).

Figure 3:
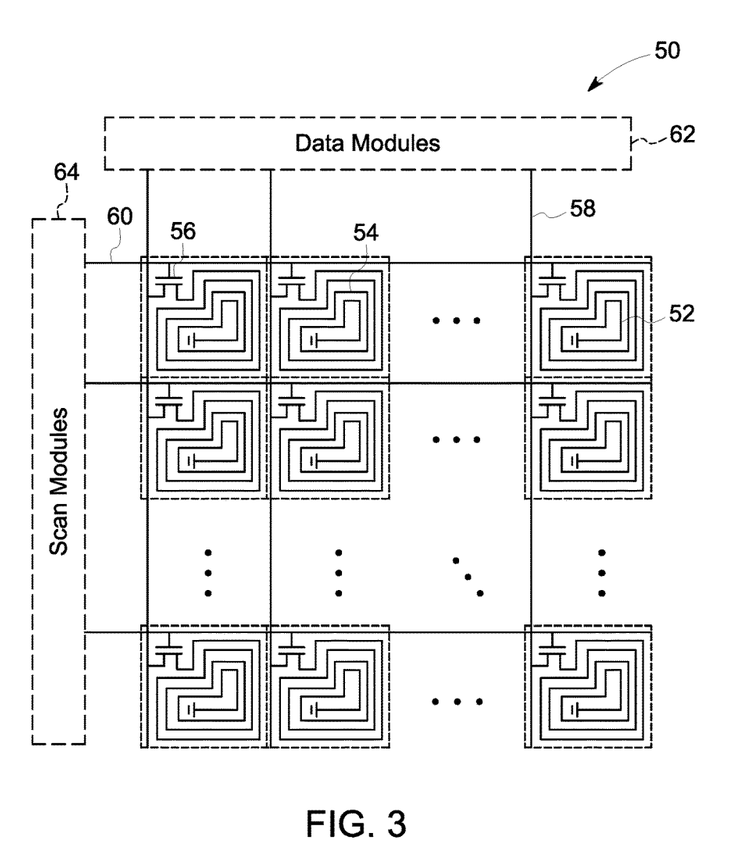
FIG. 3 is a schematic diagram of an exemplary embodiment of a 2D pixel array of the motorless real-time controllable 3D X-ray collimator of FIG. 2.

The motorless real-time controllable 3D X-ray collimator 16 further includes at least one two-dimensional (2D) pixel array 50 with a plurality of pixels 52 of thin film electric coils 54 and switching thin film field-effect transistors 56 as shown in FIG. 3. Each pixel 52 of the pixel array 50 includes a thin film electric coil 54 connected to a data line 58 and a scan line 60 through the thin film field-effect transistor 56. In an exemplary embodiment, the 2D pixel array 50 may be integrated into or attached to an inner or outer surface of the top panel 42. In an exemplary embodiment, the 2D pixel array 50 may be integrated into or attached to an inner or outer surface of the bottom panel 44. In another exemplary embodiment, the 2D pixel array 50 may be integrated into or attached to an inner or outer surface of both the top 42 and bottom 44 panels of the motorless real-time controllable 3D X-ray collimator 16.

As mentioned above, FIG. 3 illustrates a schematic diagram of an exemplary embodiment of the 2D pixel array 50 of the motorless real-time controllable 3D X-ray collimator 16 of FIG. 2. The 2D pixel array 50 includes a plurality of pixels 52 with thin film electric coils 54 and switching thin film field-effect transistors 56. Each pixel 52 includes a thin film electric coil 54 connected to a thin film field effect transistor 56 functioning as a switch and located at the intersection of a data line 58 and a scan line 60. The data lines 58 are coupled to a data module 62 and the scan lines 60 are coupled to a scan module 64. The data module 62 and scan module 64 are configured to control the pixels 52 of the pixel array and to control the motorless real-time controllable 3D X-ray collimator 16.

The pixels 52 of the pixel array 50 are organized into a plurality of rows and columns. The gates of the thin film field-effect transistors 56 in each row are connected together and coupled to a scan line 60. Similarly, the sources of the thin film field-effect transistors 56 in each column are connected together and coupled to a data line 58. The drains of the thin film field-effect transistors 56 are connected to the thin film electric coils 54. The motorless real-time controllable 3D X-ray collimator 16 and related components and circuitry of the 2D pixel array 50 receives power from the system controller 30 and related power supplies.

The present disclosure provides the ability of the motorless real-time controllable 3D X-ray collimator 16 to independently turn on and off each pixel 52 in the pixel array 50. The arbitrarily desirable shape of the X-ray beam 18 is formed through magnetic fields generated by applying current to the coils 54 of the 2D pixel array 50 thereby controlling the location of the mixture of ferromagnetic material and high X-ray attenuation material under the individual pixels 54 within the open area of the motorless real-time controllable 3D X-ray collimator 16. The application of electric current in the electric coils 54 creates a magnetic field that attracts the mixture of ferromagnetic material and high X-ray attenuation material inside the motorless real-time controllable 3D X-ray collimator 16 to the coils 54 that have current running through them, thereby blocking the X-ray beam in areas where a mixture of ferromagnetic material and high X-ray attenuation material is located under the coils 54 that have current running through them. The X-ray beam collimation is determined by the thickness of the mixture of ferromagnetic material and high X-ray attenuation material under each of the pixel coils 54.

In an exemplary embodiment, the disclosed pixel array 50 as well as the data module 62 and scan module 64 electronics are manufactured by, for example, amorphous silicon or CMOS technologies that are used to produce pixel arrays of digital X-ray detector panels. The thin film electric coils 54 may be made of electrically conductive materials such as aluminum or copper.

Please note that the pixel size of the 3D X-ray collimator 16 does not have to be aligned with the pixel size of the digital X-ray detector 24. Typically, the number of pixels in a 3D X-ray collimator is less than that of a digital X-ray detector. That is because the pixel size of a digital X-ray detector has to be small enough to achieve desired spatial resolution, while the 3D X-ray collimator only needs to distinguish regions of anatomy with significantly different densities and thicknesses.

Figure 4:
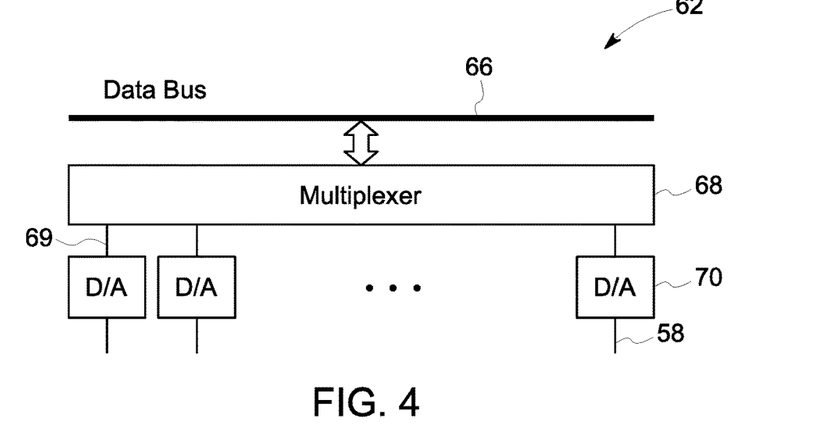
FIG. 4 is a schematic diagram of an exemplary embodiment of a data module of the 2D pixel array of FIG. 3.

FIG. 4 illustrates a schematic diagram of an exemplary embodiment of a data module 62 of the 2D pixel array 50 of FIG. 3. In an exemplary embodiment, the data module 62 may have a plurality of channels 69. Each channel 69 preferably includes a digital to analog (D/A) convertor 70 connected to a data line 58. Each of the plurality of channels 69 in the data module 62 are preferably connected to a data bus 66 through a multiplexer 68 such that each channel 69 and data line 58 may provide a different amount of electric current to each coil 54 of the pixel array 50 at the same time.

Figure 5:
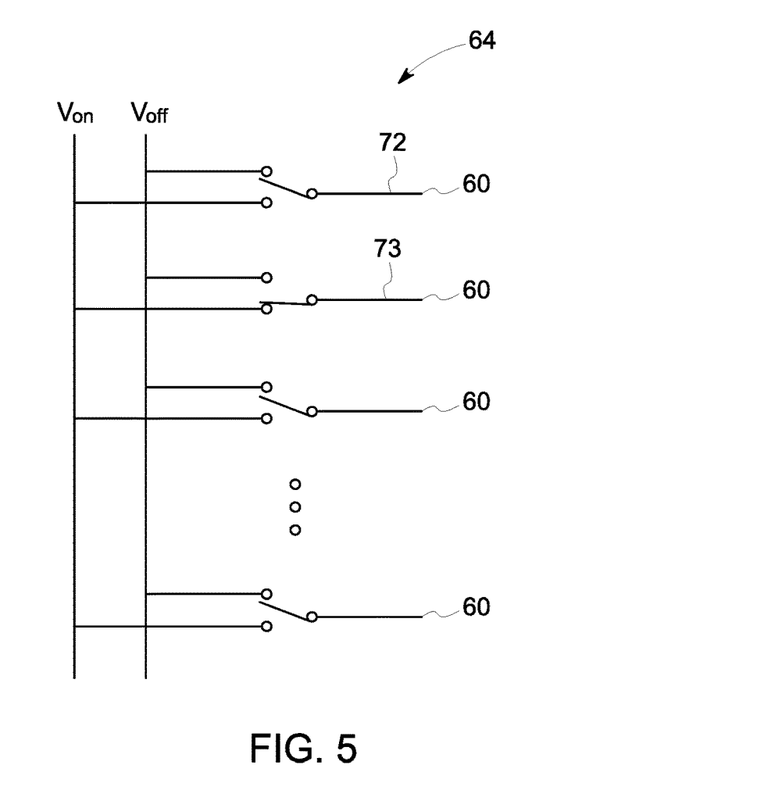
FIG. 5 is a schematic diagram of an exemplary embodiment of a scan module of the 2D pixel array of FIG. 3.

FIG. 5 illustrates a schematic diagram of an exemplary embodiment of a scan module 64 of the 2D pixel array 50 of FIG. 3. In an exemplary embodiment, the scan module 64 provides the scan lines 60 with either a positive voltage ($V_{on}$) to turn on a field-effect transistor 56, so that the electric coil 54 coupled to the field-effect transistor of a pixel 52 is connected to a corresponding data line 58 or a negative voltage ($V_{off}$) to turn off a field-effect transistor 56, so that the electric coil 54 coupled to the field-effect transistor of a pixel 52 is disconnected from a corresponding data line 58.

In the particular example shown in FIG. 5, all outputs 72 (scan lines 60) of the scan module 64 are at a negative voltage ($V_{off}$) except that the second output 73 (scan line 60) of the scan module 64 is at a positive voltage ($V_{on}$). In this case, only the pixels 52 in the second row of the pixel array 50 are connecting to the data lines 58. The pixels 52 in all other rows of the pixel array 50 are disconnected from data lines 58.

Even though all of the pixels 52 in a column of the pixel array 50 use the same data line 58, the scan module 64 selects one row of pixels 52 at a time to be connected to a data line 58. By feeding the digital to analog (D/A) converter 70 of a particular data module channel 69 with the desirable digits during the period of the time when the row of pixels 52 is selected, we can flow a different amount of electric current to the pixel array 50.

Since all pixels 52 have the same electric coil 54, the higher the electric current flowing through the electric coil, the stronger the magnetic field it produces and the more the mixture of ferromagnetic material and high X-ray attenuation material inside the real-time controllable 3D X-ray collimator 16 is attracted to the magnetic field of the coils 54 of the pixels 52. Therefore, the amount of mixture of ferromagnetic material and high X-ray attenuation material and amount of X-ray collimation is controlled by the amount of current applied to each coil 54 in the 2D pixel array 50.

Please note that the electric current flowing into the pixel array 50 row by row and the magnetic field of a pixel 52 is in an on-off-on-off pattern. As long as the magnetic field of the pixels 52 is re-freshed fast enough, the mixture of ferromagnetic material and high X-ray attenuation material is in an equilibrium condition, keeping the X-ray beam 18 from changing for a given 2D X-ray image intensity map.

Figure 6:
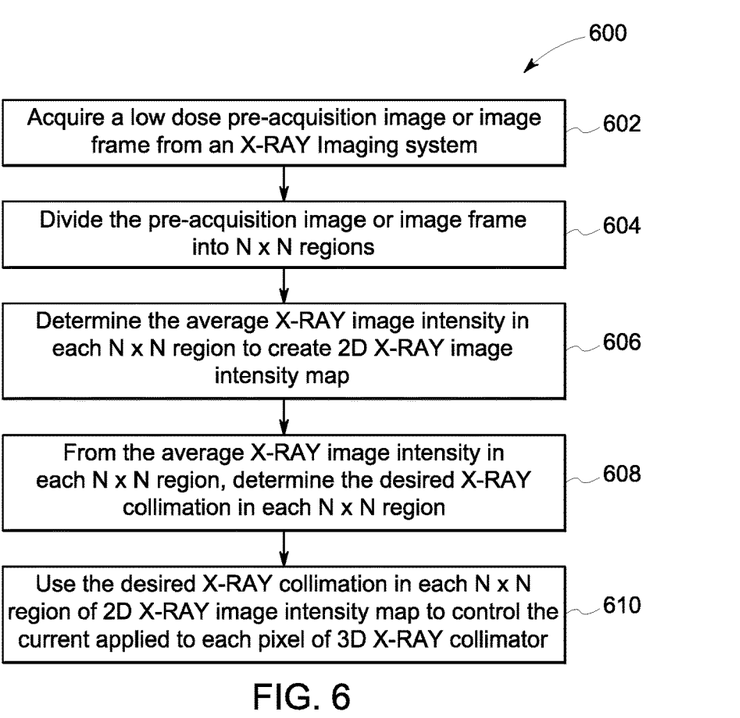
FIG. 6 is an exemplary flow diagram of an embodiment of a method for controlling a 3D X-ray collimator in real-time.

FIG. 6 illustrates an exemplary flow diagram of an embodiment of a method 600 for controlling a 3D X-ray collimator in real-time. The method 600 begins at step 602 by acquiring a pre-acquisition image in a single-shot X-ray application, such as in a radiography image acquisition, or an image frame at the beginning of a fluoroscopic image sequence from an X-ray imaging system. The next step 604 includes having an image processing system divide the pre-acquisition image or the image frame into a plurality of N×N regions. At step 606, the image processing system is used to determine the average X-ray image intensity in each of the N×N regions generating a 2D X-ray image intensity map. The 2D X-ray image intensity map is generated based on either the low dose pre-acquisition image in a single shot type of X-ray application, such as radiography imaging or an image frame at the beginning of a fluoroscopic imaging sequence. The 2D X-ray image intensity map is based on the X-ray image intensity with black meaning low X-ray image intensity and white meaning high X-ray image intensity. In other words, bone is depicted as black in the X-ray image and tissue and organs are depicted as white in the X-ray image. Image intensity is linearly proportional to the X-ray intensity. In other words, if you double the X-ray intensity you will double the X-ray image intensity. In step 608, an X-ray imaging system controller is used to determine the desired X-ray collimation in each of the N×N regions from the average X-ray image intensity determined in the 2D X-ray image intensity map. The final step of the method, step 610, includes using the desired X-ray collimation in each N×N region of the 2D X-ray image intensity map to control the current applied to each pixel or coil of the 3D X-ray collimator by the X-ray imaging system controller to control X-ray collimation to different areas of a patient's anatomy. It is important to be able to control the X-ray dose provided to different areas of anatomy of a patient undergoing an X-ray imaging acquisition or sequence. The X-ray imaging system generates an arbitrarily shaped X-ray beam according to a 2D X-ray image intensity map.

Figure 7:
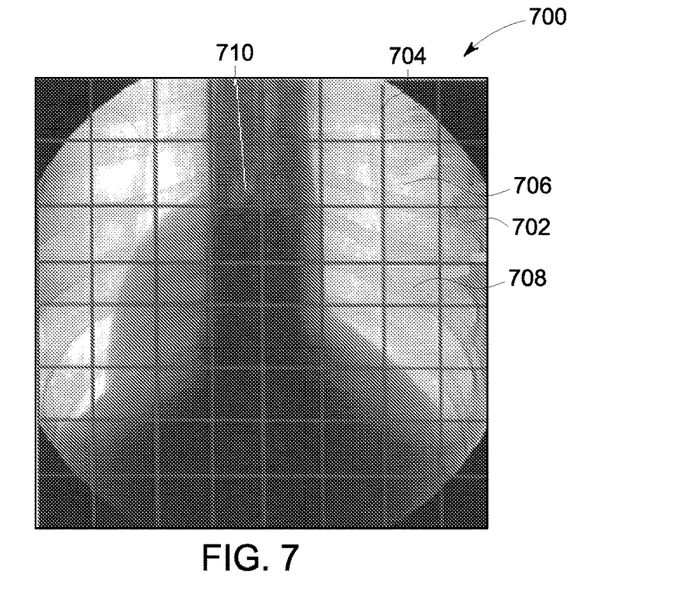
FIG. 7 is an image diagram of an exemplary embodiment of a 2D X-ray image intensity map.

FIG. 7 illustrates an image diagram of an exemplary embodiment of a 2D X-ray image intensity map 700. The 2D X-ray image intensity map 700 is generated based on either a low dose pre-acquisition image in a single shot type of X-ray application, such as radiography imaging or an image frame at the beginning of a fluoroscopic imaging sequence. The image 700 shown in FIG. 7 is an example of a low dose pre-acquisition image or an image frame from a fluoroscopic imaging sequence. The image is divided into a matrix of N×N regions. In the example shown in FIG. 7, the image is divided into a matrix of 8×8 regions 706 by horizontal lines 702 and vertical lines 704. The lighter or whiter the image in each of the regions 706, the more X-ray attenuation is required. Similarly, the darker or blacker the image in each region 706, the less X-ray attenuation is required.

The 2D X-ray image intensity map 700 is based on the X-ray image intensity with black meaning low X-ray image intensity and white meaning high X-ray image intensity. In a surgical application, bone appears as black in the X-ray image, while soft tissue appears as white in the X-ray image. This is the direct opposite in other X-ray imaging modalities, such as radiology and mammography. In these modalities, the X-ray image intensity is inverted, meaning bone appears as white in the X-ray image, while soft tissue appears as black in the X-ray image.

X-ray image intensity is linearly proportional to X-ray radiation intensity (dose). Meaning, double X-ray radiation intensity (dose) will double the X-ray image intensity. The 2D X-ray image intensity map, is used to determine which region (pixel) requires X-ray collimation. This is achieved by the total magnetic field generated by the coils in the 2D pixel array. The magnetic field strength generated by a coil is proportional to the current flowing through the coil. The shape and strength of the total magnetic field depends on the magnetic field generated by all coils. The shape and thickness of the material inside the 3D X-ray collimator is formed based on the 2D X-ray image intensity map through the magnetic field generated by the coils in the 2D pixel array.

Figure 8:
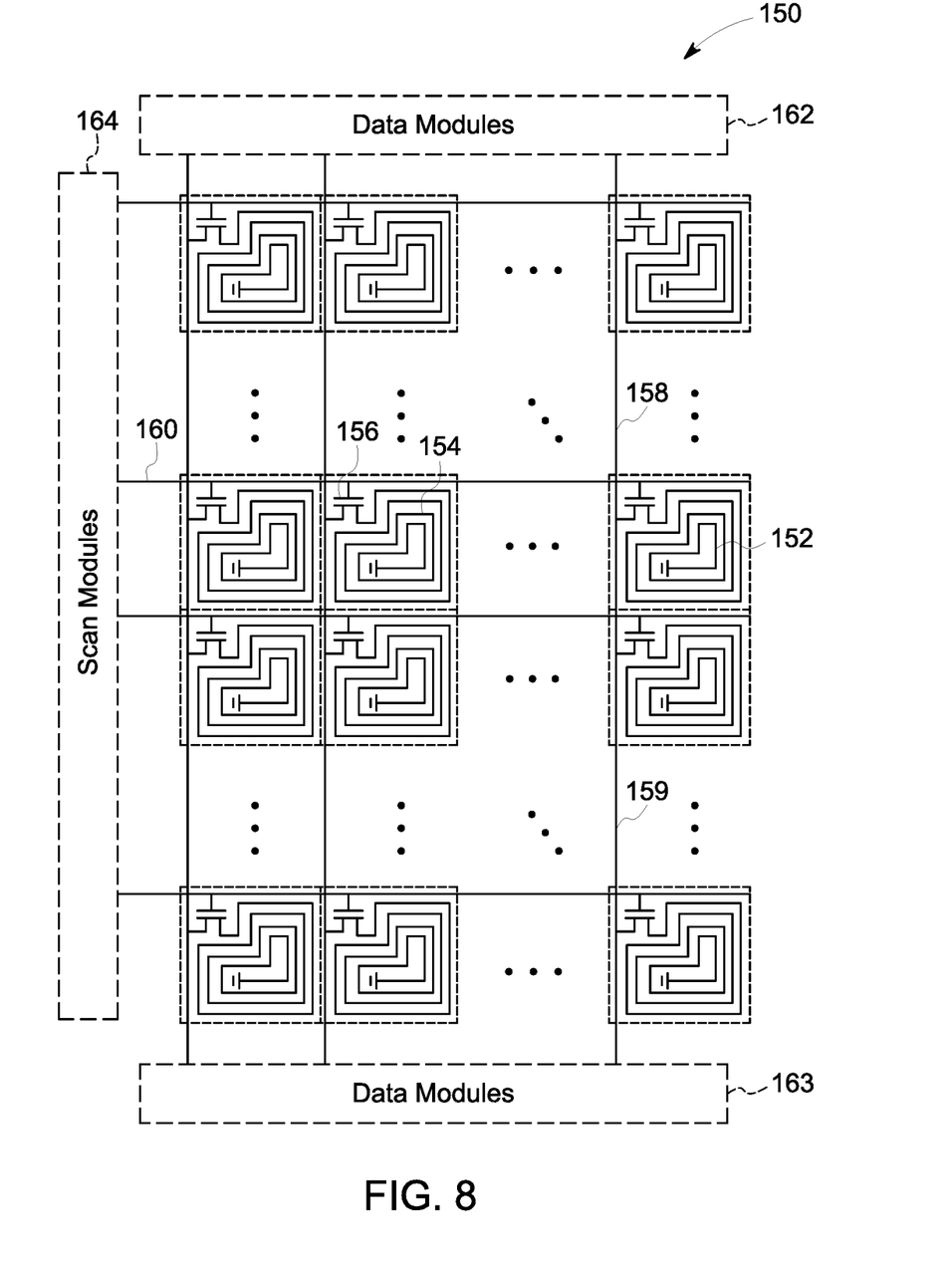
FIG. 8 is a schematic diagram of an exemplary embodiment of a 2D pixel array of a motorless real-time controllable 3D X-ray collimator.

FIG. 8 illustrates a schematic diagram of an exemplary embodiment of a 2D pixel array 150 of a real-time controllable 3D X-ray collimator. If the dimension of the pixel array 150 is too large to re-fresh the magnetic force fast enough, we can double the re-fleshing rate by cutting off the data lines 158, 159 in the middle of the array 150 and apply data modules 162, 163 on both sides of the data lines 158, 159 as shown.

The 2D pixel array 150 includes a plurality of pixels 152 with thin film electric coils 154 and switching thin film field-effect transistors 156. Each pixel 152 includes a thin film electric coil 154 connected to a thin film field effect transistor 156 functioning as a switch and located at the intersection of a data line 158 and a scan line 160. The data lines 158 are coupled to a data module 162 and the scan lines 160 are coupled to a scan module 164. The data module 162 and scan module 164 are configured to control the pixels 152 of the pixel array and to control the real-time controllable 3D X-ray collimator.

The pixels 152 of the pixel array 150 are organized into a plurality of rows and columns. The gates of the thin film field-effect transistors 156 in each row are connected together and coupled to a scan line 160. Similarly, the sources of the thin film field-effect transistors 156 in each column are connected together and coupled to a data line 158. The drains of the thin film field-effect transistors 156 are connected to the thin film electric coils 154.

Figure 9:
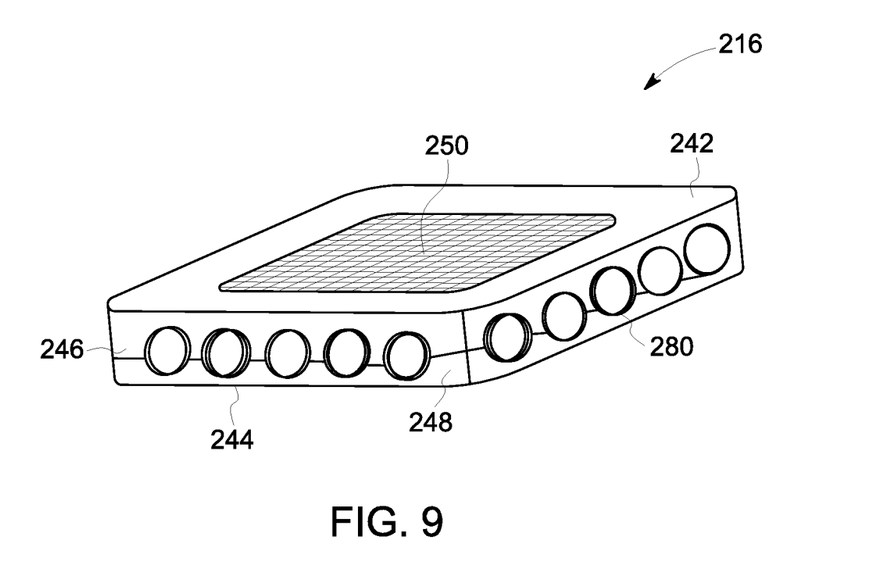
FIG. 9 is a schematic diagram of an exemplary embodiment of a motorless real-time controllable 3D X-ray collimator.

FIG. 9 illustrates a schematic diagram of an exemplary embodiment of a motorless real-time controllable 3D X-ray collimator 216. In order to control the distribution and thickness of the mixture of ferromagnetic material and high X-ray attenuation material in the motorless real-time controllable 3D X-ray collimator 216, the motorless real-time controllable 3D X-ray collimator 216 includes additional electric coils 280 positioned along the at least one sidewall 248 of the motorless real-time controllable 3D X-ray collimator 216. The stronger the magnetic field along the at least one sidewall 248 of the motorless real-time controllable 3D X-ray collimator 216 compared to those in the pixel array, the less mixture of ferromagnetic material and high X-ray attenuation material will be located inside the X-ray field in the middle of the pixel array. The required power and electrical connections between the pixel array, additional electric coils and the system controller of the X-ray imaging system can be through a wireless or wired connection.

The motorless real-time controllable 3D X-ray collimator 216 includes a top panel 242, a bottom panel 244, at least one sidewall 246 joining the top panel 242 to the bottom panel 244, and an open area 248 between the top panel 242, bottom panel 244, and at least one sidewall 246. The top panel 242 and the bottom panel 244 are spaced apart from each other by the at least one sidewall 246 and are parallel with each other. In an exemplary embodiment, the top panel 242, bottom panel 244, and at least one sidewall 246 may be made of a low X-ray attenuation material such as glass, carbon fiber, aluminum, etc. The open area 248 is at least partially filled with a mixture of ferromagnetic material and high X-ray attenuation material (not shown). The mixture of ferromagnetic material and high X-ray attenuation material blocks a portion of the X-ray beam.

As noted above, embodiments within the scope of the included program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments are described in the general context of method steps which may be implemented in one embodiment by a program product including machine-executable instructions, such as program code, for example in the form of program modules executed by machines in networked environments. Generally, program modules include routines, programs, objects, components, data structures, etc. that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Other exemplary embodiments may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the method might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

Those skilled in the art will appreciate that the embodiments disclosed herein may be applied to the formation of any medical navigation system. Certain features of the embodiments of the claimed subject matter have been illustrated as described herein, however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

As noted above, embodiments within the scope of the included program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Those skilled in the art will appreciate that the embodiments disclosed herein may be applied to the formation of any X-ray imaging system. Certain features of the embodiments of the claimed subject matter have been illustrated as described herein, however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

What is claimed is:

1. An X-ray imaging system comprising:
   an X-ray source that emits X-ray radiation;
   a motorless real-time controllable 3D X-ray collimator;
   a digital X-ray detector; and
   a system controller coupled to the X-ray source, the motorless real-time controllable 3D X-ray collimator, and the digital X-ray detector for controlling the motorless real-time controllable 3D X-ray collimator to reduce X-ray radiation dose and improve image quality;
   wherein the motorless real-time controllable 3D X-ray collimator includes a top panel; a bottom panel; at least one sidewall joining the top panel to the bottom panel; and an open area between the top panel, the bottom panel and the at least one sidewall;
   wherein the open area is at least partially filled with a mixture of ferromagnetic material and high X-ray attenuation material; and
   wherein the mixture of ferromagnetic material and high X-ray attenuation material includes iron (Fe), neodymium (Nd), tungsten (W), and lead (Pb).

2. The X-ray imaging system of claim 1, wherein the motorless real-time controllable 3D X-ray collimator arbitrarily shapes a beam of X-ray radiation.

3. The X-ray imaging system of claim 1, wherein the top panel, the bottom panel, and the at least one sidewall is made of a low X-ray attenuation material.

4. The X-ray imaging system of claim 1, wherein the mixture of ferromagnetic material and high X-ray attenuation material is a solid material.

5. The X-ray imaging system of claim 1, wherein the mixture of ferromagnetic material and high X-ray attenuation material is a liquid material.

6. The X-ray imaging system of claim 5, wherein the mixture of ferromagnetic material and high X-ray attenuation material is iron (Fe) and neodymium (Nd) suspended in mercury (Hg).

7. The X-ray imaging system of claim 1, wherein the motorless real-time controllable 3D X-ray collimator includes at least one 2D pixel array with a plurality of pixels of thin film electric coils and switching thin film field-effect transistors.

8. The X-ray imaging system of claim 7, wherein the at least one 2D pixel array is integrated into the top panel of the motorless real-time controllable 3D X-ray collimator.

9. The X-ray imaging system of claim 7, wherein the at least one 2D pixel array is integrated into the bottom panel of the motorless real-time controllable 3D X-ray collimator.

10. The X-ray imaging system of claim 7, wherein at least one 2D pixel array is integrated into the top panel of the motorless real-time controllable 3D X-ray collimator and at least one 2D pixel array is integrated into the bottom panel of the motorless real-time controllable 3D X-ray collimator.

11. The X-ray imaging system of claim 1, further comprising a 2D X-ray image intensity map generated from a pre-acquisition image in a single shot radiography application or an image frame at the beginning of a fluoroscopic sequence in a fluoroscopy application.

12. The X-ray imaging system of claim 1, wherein the motorless real-time controllable 3D X-ray collimator further includes a plurality of electric coils coupled to the at least one sidewall of the motorless real-time controllable 3D X-ray collimator.

13. A motorless real-time controllable 3D X-ray collimator comprising:
    a top panel;
    a bottom panel;
    at least one sidewall joining the top panel to the bottom panel;
    an open area between the top panel, bottom panel, and at least one sidewall; and
    at least one 2D pixel array coupled to at least one of the top panel and the bottom panel, the at least one 2D pixel array having a plurality of pixels of thin film electric coils and switching thin film field-effect transistors;
    wherein the open area is at least partially filled with a mixture of ferromagnetic material and high X-ray attenuation material; and
    wherein the mixture of ferromagnetic material and high X-ray attenuation material includes iron (Fe), neodymium (Nd), tungsten (W), and lead (Pb).

14. The motorless real-time controllable 3D X-ray collimator of claim 13, wherein the mixture of ferromagnetic material and high X-ray attenuation material is a mixture of iron (Fe) and neodymium (Nd) suspended in mercury (Hg).

15. The motorless real-time controllable 3D X-ray collimator of claim 13, wherein the motorless real-time controllable 3D X-ray collimator is controlled with the use of a 2D X-ray image intensity map that is generated from an X-ray imaging system.

16. A method of controlling a 3D X-ray collimator in real-time, the method comprising the steps of:
    acquiring a pre-acquisition image or an image frame from an X-ray imaging system;
    dividing the pre-acquisition image or image frame into N×N regions through the use of an image processing system;
    determining the average X-ray image intensity in each N×N region to create a 2D X-ray image intensity map;
    determining the desired X-ray collimation in each N×N region from the average X-ray image intensity in each N×N region; and
    using the desired X-ray collimation in each N×N region of the 2D X-ray image intensity map to control current applied to at least one coil of the 3D X-ray collimator.

* * * * *